United States Patent
Amakawa et al.

(10) Patent No.: US 6,984,758 B2
(45) Date of Patent: Jan. 10, 2006

(54) PURIFICATION OF 1,3-BIS(AMINOMETHYL)CYCLOHEXANE BY DISTILLATION

(75) Inventors: Kazuhiko Amakawa, Niigata (JP); Kuniaki Muneyasu, Niigata (JP); Hiroshi Watanabe, Niigata (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 0 days.

(21) Appl. No.: 11/080,548

(22) Filed: Mar. 16, 2005

(65) Prior Publication Data
US 2005/0215824 A1    Sep. 29, 2005

(30) Foreign Application Priority Data
Mar. 29, 2004 (JP) .............................. 2004-094366

(51) Int. Cl.
*C07C 211/00* (2006.01)
(52) U.S. Cl. .................. 564/455; 564/449; 564/451
(58) Field of Classification Search ................ 564/455, 564/449, 451
See application file for complete search history.

(56) References Cited

U.S. PATENT DOCUMENTS 3,998,881 A    12/1976   Butte, Jr. et al.
5,741,928 A *  4/1998    Kobayashi et al. ......... 564/449

FOREIGN PATENT DOCUMENTS

DE   25 51 055 A1    5/1976
JP   49-042645 A2 *  4/1974

OTHER PUBLICATIONS

European Search Report, for Application No. 05101990.9-2103 PCT, dated Aug. 3, 2005.

* cited by examiner

*Primary Examiner*—Samuel Barts
(74) *Attorney, Agent, or Firm*—Antonelli, Terry, Stout and Kraus, LLP.

(57) ABSTRACT

A crude liquid containing 1,3-bis(aminomethyl)cyclohexane and a high-boiling component having a boiling point higher than that of 1,3-bis(aminomethyl)cyclohexane is distilled. By controlling the distillation conditions, the high-boiling component is prevented from entering into a distilled 1,3-bis(aminomethyl)cyclohexane and the content of a low-boiling component in the distilled 1,3-bis(aminomethyl)cyclohexane is minimized.

6 Claims, No Drawings

PURIFICATION OF 1,3-BIS(AMINOMETHYL)CYCLOHEXANE BY DISTILLATION

BACKGROUND OF THE INVENTION

1. Field of the Invention

The present invention relates to a method of purifying 1,3-bis(aminomethyl)cyclohexane (1,3-BAC) by distillation, more specifically, relates to a method of purifying 1,3-BAC which includes a step of distilling a crude liquid containing 1,3-BAC to remove a high-boiling component having a boiling point higher than that of 1,3-BAC thereby to obtain a purified 1,3-BAC. 1,3-BAC is a useful compound that has been widely used in industrial applications such as resin curing agents, raw materials for polyamide, raw materials for isocyanate, rubber chemicals, paper processing agents, fiber treating agents and cleaning agents.

2. Description of the Prior Art

As the production methods of 1,3-BAC, there are known a method of hydrogenating the benzene ring of m-xylylenediamine (JP 42-26783B, JP 50-126638A, JP 51-7659B, JP 54-16452A and JP 8-143514A), a method of simultaneously hydrogenating the benzene ring and nitrile group by the reaction of isophthalonitrile and hydrogen (JP 51-68540A and JP 10-76160A), a method of hydrogenating dicyanocyclohexane (Japanese Patent No. 2718740, JP 41-21338B and JP 2001-187765 A), etc.

As to the purification by distillation of a crude reaction product liquid containing 1,3-BAC obtained in the methods described above, JP 49-42645A teaches that the production of low boiling compounds such as methylene cyclohexylmethylamine can be avoided by coexisting nitrogen, ammonia or water during maintaining 1,3-BAC under heating conditions.

In the method taught by JP 49-42645A where water is coexisted, the water should be finally removed to obtain a high purity 1,3-BAC. If ammonia is coexisted, the ammonia is dissolved in the distilled 1,3-BAC to generate pungent odor. When nitrogen is coexisted, the nitrogen introduced into the 1,3-BAC-containing liquid placed at the column bottom is finally exhausted into a vacuum line after passing through the internal portion of distillation column and column top. Therefore, the vapor load in the inside of column is increased to reduce the treating capacity of distillation column. Also, the vacuum apparatus with higher capacity is needed because the load of vacuum line is increased. In addition, the loss of 1,3-BAC is increased because 1,3-BAC accompanies with nitrogen to escape into the vacuum line.

The inventors have conducted the distillation of a 1,3-BAC-containing liquid according to the method taught by JP 49-42645A. The results of distillation varied depending on the starting liquid to be distilled and the distillation conditions. In some cases, a large amount of low-boiling components were generated by the degradation of 1,3-BAC, and the generated low-boiling components contaminated the distilled 1,3-BAC. Thus, the method proposed by JP 49-42645A failed to sufficiently prevent the decomposition of 1,3-BAC.

SUMMARY OF THE INVENTION

The present invention is directed to provide a simple and industrially advantageous method of purifying a 1,3-BAC-containing liquid by distillation, which is capable of providing a purified 1,3-BAC that is free from a high-boiling component having a boiling point higher than that of 1,3-BAC and less contaminated with a low-boiling component.

The inventors have made extensive research on the contamination of the distilled 1,3-BAC with low-boiling components. As a result, it has been found that the low-boiling contaminant is not methylenecyclohexylmethylamine which is taught by JP 49-42645A as a main component of the decomposed products of 1,3-BAC, but 3-azabicyclo[3.3.1]nona-2-ene (ABN). It has been not known in the art that ABN is generated during the purification operation by distillation to contaminate the distillate, and no means for solving such a problem is hitherto proposed.

The inventors have further made extensive research on the distillation of a crude liquid containing 1,3-BAC. As a result, it has been found that 1,3-BAC is mainly degraded at the bottom of distillation column into ABN and that the degree of degradation of 1,3-BAC closely depends on the concentrations of specific metal components in the bottom liquid and the operating conditions of distillation. On the basis of these findings, the inventors have further found that the above problem is solved by controlling the bottom liquid under specific conditions during the distillation and reached the present invention.

Thus, the invention relates to a method of purifying 1,3-BAC which includes a step of distilling a crude liquid containing 1,3-BAC and a high-boiling component having a boiling point higher than that of 1,3-BAC under conditions satisfying the following requirements A and B:

(A) controlling a concentration of each of ruthenium, rhodium, palladium, platinum, cobalt and nickel which are contained in a bottom liquid placed in a distillation apparatus to less than 2 ppm by weight; and (B) distilling the bottom liquid under conditions satisfying the flowing formula 1:

$$\ln(c \cdot V/D) < (10000/(T+273)) - 17.2 \qquad (1)$$

wherein c is a concentration (% by weight) of 1,3-BAC in the bottom liquid, V is a hold up amount (kg) of the bottom liquid, D is a distillation speed (kg/h) representing an hourly amount of a purified 1,3-BAC recovered from a top of the distillation apparatus, and T is a temperature (° C.) of the bottom liquid, thereby obtaining a purified 1,3-BAC that is free from the high-boiling component.

DETAILED DESCRIPTION OF THE INVENTION

The high-boiling component having a boiling point higher than that of 1,3-BAC which is contained in the 1,3-BAC-containing crude liquid to be distilled may include raw materials and solvent for synthesizing 1,3-BAC and high-boiling by-products, although not limited thereto. The 1,3-BAC-containing crude liquid to be distilled may further contain a low-boiling component having a boiling point lower than that of 1,3-BAC, for example, the solvent used in the synthesis of 1,3-BAC and low-boiling products by-produced in the synthesis of 1,3-BAC. 1,3-BAC may be a mixture with isomers such as 1,4-BAC. In such case, a distilled 1,3-BAC may contain a component described above.

1,3-BAC is produced by the hydrogenation of benzene ring of m-xylylenediamine, the hydrogenation of benzene ring and nitrile group of isophthalonitrile, or the hydrogenation of dicyanocyclohexane. The 1,3-BAC-containing crude liquid to be distilled may be the reaction product liquid of these reactions. The reaction production liquid may be subjected, in advance, to vacuum distillation, etc. to remove a part of low-boiling components having a boiling point lower than that of 1,3-BAC.

The distillation of the invention can be performed by using a known distillation apparatus. The apparatus is suitably selected from various distillation apparatuses such as a distillation column equipped with a fractionating portion including plates, packed beds, etc. and a simple distillation apparatus according to the chemical composition of 1,3-BAC-containing crude liquid to be distilled. The distilled 1,3-BAC free from the high-boiling components is generally recovered from the top of distillation apparatus.

The distillation is conducted while controlling the concentration of each of ruthenium, rhodium, palladium, platinum, cobalt and nickel in the bottom liquid of distillation apparatus to less than 2 ppm by weight (inclusive of zero), preferably 1 ppm by weight or less, and more preferably 0.5 ppm by weight or less. The generation of ABN due to the degradation of 1,3-BAC is accelerated with increasing concentrations of these metal components. If the concentration of each metal component is 2 ppm by weight or more, the distilled 1,3-BAC recovered from the column top will be contaminated with a considerable amount of ABN.

In many cases, the above metal components are derived from the catalyst used in the production of 1,3-BAC. 1,3-BAC is generally produced by the hydrogenation of the 1,3-BAC precursor such as m-xylylenediamine, isophthalonitrile and 1,3-dicyanocyclohexane in the presence of a catalyst containing a metal component such as ruthenium, rhodium, palladium, platinum, cobalt and nickel. If these metal components derived from catalyst remain in the 1,3-BAC-containing crude liquid which is supplied to the distillation step after the production of 1,3-BAC by hydrogenation, the metal components are concentrated in the bottom liquid during the distillation because the metal components are usually nonvolatile. If the concentration of each metal component reaches 2 ppm by weight or more, the degradation of 1,3-BAC will increase.

The metal components are used as the catalyst in the form of a homogeneous complex catalyst, a fine powdery solid catalyst for slurry bed reactors, a shaped solid catalyst such as pellets for fixed bed reactors, etc. To prevent the metal components from entering into the 1,3-BAC-containing crude liquid to be supplied into the distillation step, it is necessary to sufficiently remove the metal components before supplying into the distillation step, for example, by extraction when the homogeneous complex catalyst is used or by filtration or centrifugation when the fine powdery solid catalyst is used. In case of using the fixed bed shaped catalyst, fine powders containing the metal components generated from the shaped catalyst may, in some cases, enter into the 1,3-BAC-containing crude liquid especially at the initial stage of using the catalyst. Therefore, a care should be taken. Even if the catalyst is in a solid catalyst, the metal components may be dissolved and enter into the 1,3-BAC-containing crude liquid according to the chemical types and physical states of the catalyst and the reaction conditions. Therefore, it is preferred to suitably select the chemical type and reaction conditions to minimize the dissolution of the metal components.

The concentration of each of ruthenium, rhodium, palladium, platinum, cobalt and nickel is determined by inductively coupled plasma emission spectroscopy (ICP analysis) or atomic absorption spectroscopy.

The distillation of the invention is carried out under the conditions satisfying the following formula 1:

$$\ln(c \cdot V/D) < (10000/(T+273)) - 17.2 \quad (1)$$

wherein c is the concentration (% by weight) of 1,3-BAC in the bottom liquid, V is the hold up amount (kg) of the bottom liquid, D is the distillation speed (kg/h) representing the hourly amount of purified 1,3-BAC recovered from the top of the distillation apparatus, and T is the temperature (° C.) of the bottom liquid. The value of $\ln(c \cdot V/D)$ is preferably from −3.0 to 5.0, and more preferably from −2.0 to 3.0.

To attain the conditions satisfying the formula 1, it is preferred to make the concentration of 1,3-BAC in the bottom liquid low, to make the ratio of the hold up of the bottom liquid to the distillation speed low, and to make the temperature of the bottom liquid low. After repeated experimentation of distillation under different conditions, the conditions defined by the formula 1 has been empirically found.

The distillation is performed in either of batch-wise manner or continuous manner. The distillation in continuous manner is industrially preferred. As described above, the ratio of the hold up of the bottom liquid to the distillation speed is preferably low in the invention. Since the hold up of the bottom liquid tends to be large in the batch-wise distillation, the continuous distillation is preferably employed.

It is preferred in the invention that the weight ratio of the hold up of the bottom liquid in the distillation apparatus to the distillation speed of 1,3-BAC is low. The hold up of the bottom liquid referred to herein is the sum of the weight of the liquid present at the bottom of distillation apparatus, the weight of the liquid present in the reboiler, pump and lines which are equipped around the bottom of distillation apparatus. The distillation speed referred to herein is the weight of distillate recovered from the top of distillation apparatus per one hour. To make the weight ratio of the hold up of the bottom liquid to the distillation speed of 1,3-BAC low, it is effective to reduce the hold up of the bottom liquid, this being attained, for example in the continuous distillation, by reducing the depth of the bottom of distillation apparatus thereby to reduce the capacity or by designing the shape of the bottom and the surrounding equipments such as boiler so as to have smaller hold up amounts. In view of reducing the hold up of the bottom liquid, a thin film distillation apparatus is preferably used.

In the continuous distillation, the temperature and the concentration of 1,3-BAC of the bottom liquid can be controlled by selecting the distillation conditions such as operating pressure and the discharging amount of the bottom liquid. The concentration (c) of 1,3-BAC in the bottom liquid in the distillation apparatus is preferably 30% by weight or less, more preferably from 0.1 to 30% by weight, and still more preferably from 0.5 to 25% by weight. The temperature (T) of the bottom liquid is preferably from 50 to 210° C., more preferably from 60 to 200° C., and still more preferably from 70 to 190° C. The ratio of the hold up (V) of the bottom liquid to the distillation speed (D), V/D, is preferably from 0.01 to 5 h, and more preferably 0.03 to 3 h. The distillation is performed at reduced pressure preferably at 0.05 to 20 kPa, more preferably at 0.1 to 15 kPa, and still more preferably 0.1 to 10 kPa.

When the concentrations of the metal components in the bottom liquid, the concentration of 1,3-BAC, the distillation speed, the hold up of the bottom liquid, and the temperature of the bottom liquid change during the distillation as in the case of the batch-wise distillation, the average value of each parameter is determined every one hour during the distillation. Then, each parameter is regulated so as to meet the requirement of formula 1. By conducting the distillation in this manner, the effect of the invention is attained sufficiently.

According to the invention, the content of ABN in the distilled 1,3-BAC is reduced to 0.1% by weight of 1,3-BAC. When the 1,3-BAC-containing crude liquid to be distilled contains substantially no low-boiling component having a boiling point lower than that of 1,3-BAC, 1,3-BAC with a purity as high as 99.9% by weight or more can be obtained. 1,3-BAC with a higher purity is recently demanded as the raw material for the production of high quality polyamide resin. The purification method of the invention is capable of providing a high purity 1,3-BAC that meets such a demand.

The present invention will be explained in more detail by reference to the following example which should not be construed to limit the scope of the present invention.

EXAMPLE 1

By hydrogenating m-xylylenediamine (available from Mitsubishi Gas Chemical Company, Inc., hereinafter referred to as "MXDA") in the presence of an alumina catalyst supporting 2% by weight of ruthenium, 1,3-bis (aminomethyl)cyclohexane (1,3-BAC) was produced. The hydrogenation was performed in a fixed bed reactor while supplying the starting liquid and hydrogen from the top of the reactor under the following conditions.

Hydrogenation pressure: 10 MPa
Hydrogenation temperature: 105° C.
Composition of starting liquid: MXDA/1,3-BAC=5/95 (by weight)
Liquid hourly space velocity (LHSV): 1.0 h$^{-1}$
Gas hourly space velocity (GHSV): 400 h$^{-1}$ By removing the low-boiling component having a boiling point lower than that of 1,3-BAC from the reaction production liquid by vacuum distillation, a 1,3-BAC-containing crude liquid having a chemical composition of 1,3-BAC/MXDA/high-boiling component=97.7/1.8/0.5 (% by weight) was obtained. The obtained crude liquid was supplied into the middle of a dumped-packing metal distillation column with 16 theoretical plates and continuously distilled at a column top pressure of 5 kPa. The chemical composition of the bottom liquid during the distillation was 1,3-BAC/MXDA/high-boiling component= 5/76/19 (% by weight) at a bottom liquid temperature of 172° C. The weight ratio of the hold up of the bottom liquid to the distillation speed was 1.9. These distillation conditions met the requirement of formula 1 as calculated below.

Left side: $\ln(c \cdot V/D)=\ln(5\times1.9)=2.25$

Right side: $(10000/(T+273))-17.2=(10000/(172+273))-17.2=5.27$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.9% by weight or more and the content of ABN was 45 ppm by weight.

EXAMPLE 2

The distillation was conducted in the same manner as in Example 1 except for changing the bottom liquid temperature to 169° C. The chemical composition of the bottom liquid during the distillation was 1,3-BAC/MXDA/high-boiling component=10/72/18 (% by weight). The weight ratio of the hold up of the bottom liquid to the distillation speed was 1.9. The distillation conditions met the requirement of formula 1 as calculated below.

Left side: $\ln(c \cdot V/D)=\ln(10\times1.9)=2.94$

Right side: $(10000/(T+273))-17.2=(10000/(169+273))-17.2=5.42$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.9% by weight or more and the content of ABN was 80 ppm by weight.

EXAMPLE 3

The distillation was conducted in the same manner as in Example 2 except for reducing the supplying speed of the 1,3-BAC-containing liquid by half. The chemical composition of the bottom liquid was 1,3-BAC/MXDA/high-boiling component=10/72/18 (% by weight) at a bottom liquid temperature of 169° C. The weight ratio of the hold up of the bottom liquid to the distillation speed was 3.8. The distillation conditions met the requirement of formula 1 as calculated below.

Left side: $\ln(c \cdot V/D)=\ln(10\times3.8)=3.64$

Right side: $(10000/(T+273))-17.2=(10000/(169+273))-17.2=5.42$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.9% by weight or more and the content of ABN was 192 ppm by weight.

EXAMPLE 4

By hydrogenating isophthalonitrile (available from Mitsubishi Gas Chemical Company, Inc., hereinafter referred to as "IPN") in the presence of an alumina catalyst supporting 2% by weight of ruthenium, 1,3-BAC was produced. The hydrogenation was performed in a fixed bed reactor while supplying the starting liquid and hydrogen from the top of the reactor under the following conditions.

Hydrogenation pressure: 15 MPa
Hydrogenation temperature: 120° C.
Composition of starting liquid: IPN/dioxane/ammonia=5/60/35 (by weight)
LHSV: 0.4 h$^{-1}$
GHSV: 400 h$^{-1}$ By removing ammonia, dioxane and by-produced low-boiling component from the reaction production liquid by distillation, a 1,3-BAC-containing crude liquid having a chemical composition of 1,3-BAC/MXDA/high-boiling component=88/8/4 (% by weight) was obtained. The obtained crude liquid was supplied into the middle of a dumped-packing metal distillation column with 16 theoretical plates and continuously distilled at a column top pressure of 5 kPa. The chemical composition of the bottom liquid during the distillation was 1,3-BAC/MXDA/high-boiling component=5/63/32 (% by weight) at a bottom liquid temperature of 178° C. The weight ratio of the hold up of the bottom liquid to the distillation speed was 1.9. These distillation conditions met the requirement of formula 1 as calculated below.

Left side: $\ln(c \cdot V/D) = \ln(5 \times 1.9) = 2.25$

Right side: $(10000/(T+273)) - 17.2 = (10000/(178+273)) - 17.2 = 4.97$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.9% by weight or more and the content of ABN was 180 ppm by weight.

COMPARATIVE EXAMPLE 1

The distillation was conducted in the same manner as in Example 3 except for changing the column top pressure to 21 kPa and the bottom liquid temperature to 210° C. The chemical composition of the bottom liquid during the distillation was 1,3-BAC/MXDA/high-boiling component=10/72/18 (% by weight). The weight ratio of the hold up of the bottom liquid to the distillation speed was 3.8. The distillation conditions failed to meet the requirement of formula 1 as calculated below.

Left side: $\ln(c \cdot V/D) = \ln(10 \times 3.8) = 3.64$

Right side: $(10000/(T+273)) - 17.2 = (10000/(210+273)) - 17.2 = 3.59$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.8% by weight and the content of ABN was 1090 ppm by weight.

COMPARATIVE EXAMPLE 2

The 1,3-BAC-containing crude liquid of 1,3-BAC/MXDA/high-boiling component=97.7/1.8/0.5 (% by weight) obtained in Example 1 was distilled in batch-wise manner. A distillation apparatus having a 5-L flask (column bottom) and a dumped-packing column with 7 theoretical plates was used. The 1,3-BAC-containing crude liquid (3 kg) was charged into the column bottom and distilled under a column top pressure of 5 kPa. After the column top temperature and column bottom temperature became stable, 0.06 kg of fraction mainly consisting of 1,3-BAC was collected over one hour.

During the distillation, the average temperature of the bottom liquid was 141° C. and the average 1,3-BAC concentration of the bottom liquid was 97.6% by weight. The hold up of the bottom liquid was 2.97 kg in average. The weight ratio of the hold up of the bottom liquid to the distillation speed was 49.5. These distillation conditions failed to meet the requirement of formula 1 as calculated below.

Left side: $\ln(c \cdot V/D) = \ln(97.6 \times 49.5) = 8.48$

Right side: $(10000/(T+273)) - 17.2 = (10000/(141+273)) - 17.2 = 6.95$

The concentration of metal component in the bottom liquid determined by ICP analysis was 0.1 ppm by weight or lower for all of ruthenium, rhodium, palladium, platinum, cobalt and nickel. The gas chromatographic analysis of the distillate recovered from the top of column showed that the purity of 1,3-BAC was 99.8% by weight and the content of ABN was 1150 ppm by weight.

COMPARATIVE EXAMPLE 3

By hydrogenating MXDA in the presence of a carbon catalyst supporting 5% by weight of ruthenium, 1,3-BAC was produced. The hydrogenation was performed in a slurry bed reactor by charging MXDA and ammonia in a weight ratio of 20/80 and the catalyst in 5% by weight of the charged MXDA under a reaction pressure of 10 MPa and a reaction temperature of 120° C. The rate of hydrogen consumption was monitored and the reaction was stopped at the time when hydrogen was no longer consumed. After reducing the pressure to atmospheric pressure, ammonia was removed from the crude reaction product liquid by evaporation and the catalyst was removed by filtration through a filter paper. Then, the low-boiling component having a boiling point lower than that of 1,3-BAC was removed by vacuum distillation to obtain a 1,3-BAC-containing crude liquid having a chemical composition of 1,3-BAC/MXDA/high-boiling component=98.2/0.1/1.7 (% by weight) was obtained. The obtained crude liquid was supplied into the middle of a dumped-packing metal distillation column with 16 theoretical plates and continuously distilled at a column top pressure of 5 kPa. The chemical composition of the bottom liquid during the distillation was 1,3-BAC/MXDA/high-boiling component=15/5/80 (% by weight) at a bottom liquid temperature of 183° C. The weight ratio of the hold up of the bottom liquid to the distillation speed was 1.9. These distillation conditions met the requirement of formula 1 as calculated below.

Left side: $\ln(c \cdot V/D) = \ln(15 \times 1.9) = 3.35$

Right side: $(10000/(T+273)) - 17.2 = (10000/(183+273)) - 17.2 = 4.73$

The concentration of ruthenium in the bottom liquid determined by ICP analysis was 3.1 ppm by weight. The concentration for each of rhodium, palladium, platinum, cobalt and nickel was 0.1 ppm by weight or less. The gas chromatographic analysis of the distillate recovered from the top of column showed that the purity of 1,3-BAC was 99.8% by weight or more and the content of ABN was 1230 ppm by weight.

The high purity 1,3-BAC obtained by the invention is a useful compound that has been widely used in industrial applications such as resin curing agents, raw materials for polyamide, raw materials for isocyanate, rubber chemicals, paper processing agents, fiber treating agents and cleaning agents. By distilling a 1,3-BAC-containing crude liquid according to the purification method of the invention, a purified 1,3-BAC that is free from the high-boiling component having a boiling point higher than that of 1,3-BAC and less contaminated with ABN is obtained easily. Therefore, the invention is of great industrial value.

What is claimed is:

1. A method of purifying 1,3-bis(aminomethyl)cyclohexane which comprises a step of distilling a crude liquid containing 1,3-bis(aminomethyl)cyclohexane and a high-boiling component having a boiling point higher than that of 1,3-bis(aminomethyl)cyclohexane under conditions satisfying the following requirements A and B:
  (A) controlling a concentration of each of ruthenium, rhodium, palladium, platinum, cobalt and nickel which are contained in a bottom liquid placed in a distillation apparatus to less than 2 ppm by weight; and
  (B) distilling the bottom liquid under conditions satisfying the following formula 1:

$$\ln(c \cdot V/D) < (10000/(T+273)) - 17.2 \qquad (1)$$

wherein c is a concentration (% by weight) of 1,3-bis(aminomethyl)cyclohexane in the bottom liquid, V is a hold up amount (kg) of the bottom liquid, D is a distillation speed (kg/h) and T is a temperature (° C.) of the bottom liquid, thereby obtaining a purified 1,3-bis(aminomethyl)cyclohexane which is free from the high-boiling component.

2. The method according to claim 1, wherein the crude liquid to be distilled is a reaction production liquid obtained by a hydrogenation of a precursor for 1,3-bis(aminomethyl)cyclohexane in the presence of a catalyst containing at least one metal selected from the group consisting of ruthenium, rhodium, palladium, platinum, cobalt and nickel.

3. The method according to claim 2, wherein the precursor for 1,3-bis(aminomethyl)cyclohexane is m-xylylenediamine or isophthalonitrile.

4. The method according to claim 2, wherein the crude liquid to be distilled is obtained by removing a low-boiling component having a boiling point lower than that of 1,3-bis(aminomethyl)cyclohexane from the reaction production liquid.

5. The method according to according to claim 1, wherein the distillation is performed in continuous manner.

6. The method according to according to claim 1, wherein a content of 3-azabicyclo[3.3.1]nona-2-ene in the purified 1,3-bis(aminomethyl)cyclohexane is 0.1% by weight or less.

* * * * *